(12) United States Patent
Greenberg et al.

(10) Patent No.: US 7,160,318 B2
(45) Date of Patent: Jan. 9, 2007

(54) MODULAR STENT GRAFT ASSEMBLY AND USE THEREOF

(75) Inventors: Roy K. Greenberg, Bratenahl, OH (US); Jason A. Mead, Indianapolis, IN (US)

(73) Assignee: Cook Incorporated, Bloomington, IN (US)

( * ) Notice: Subject to any disclaimer, the term of this patent is extended or adjusted under 35 U.S.C. 154(b) by 429 days.

(21) Appl. No.: 10/104,672

(22) Filed: Mar. 22, 2002

(65) Prior Publication Data
US 2002/0198587 A1 Dec. 26, 2002

Related U.S. Application Data

(60) Provisional application No. 60/279,329, filed on Mar. 28, 2001.

(51) Int. Cl.
*A61F 2/06* (2006.01)

(52) U.S. Cl. .................................... 623/1.13

(58) Field of Classification Search ............... 623/1.13, 623/1.16, 1.15, 1.3, 1.31, 1.35
See application file for complete search history.

(56) References Cited

U.S. PATENT DOCUMENTS

| 5,324,304 | A |  | 6/1994 | Rasmussen |  |
|---|---|---|---|---|---|
| 5,387,235 | A |  | 2/1995 | Chuter |  |
| 5,443,497 | A |  | 8/1995 | Venbrux |  |
| 5,456,713 | A |  | 10/1995 | Chuter |  |
| 5,562,697 | A |  | 10/1996 | Christiansen |  |
| 5,562,724 | A |  | 10/1996 | Vorwerk et al. |  |
| 5,562,726 | A |  | 10/1996 | Chuter |  |
| 5,683,449 | A | * | 11/1997 | Marcade | 128/898 |
| 5,693,084 | A |  | 12/1997 | Chuter |  |
| 5,720,776 | A |  | 2/1998 | Chuter et al. |  |
| 5,755,777 | A |  | 5/1998 | Chuter |  |
| 5,824,037 | A | * | 10/1998 | Fogarty et al. | 623/1.13 |
| 6,102,938 | A |  | 8/2000 | Evans et al. |  |
| 6,110,198 | A |  | 8/2000 | Fogarty et al. |  |
| 6,162,246 | A | * | 12/2000 | Barone | 623/1.35 |
| 6,325,819 | B1 |  | 12/2001 | Pavcnik et al. |  |
| 6,325,820 | B1 | * | 12/2001 | Khosravi et al. | 623/1.13 |
| 6,409,756 | B1 | * | 6/2002 | Murphy | 623/1.35 |

FOREIGN PATENT DOCUMENTS

| WO | 9853761 | 12/1998 |
|---|---|---|
| WO | 0061034 | 10/2000 |

* cited by examiner

*Primary Examiner*—Corrine McDermott
*Assistant Examiner*—William H Matthews
(74) *Attorney, Agent, or Firm*—Richard J. Godlewski

(57) ABSTRACT

A modular stent graft assembly (10) for repairing a ruptured abdominal aorta aneurysm (90) and having an aortic section tubular graft (12) and an iliac section tubular graft (14). The aortic section graft has a proximal attachment stent (32) thereon for suprarenal attachment of the assembly (10) to the aorta. A proximal end portion (50) of the iliac section graft (14) underlies the distal end portion (28) of the aortic graft (12) and presses outwardly thereagainst forming a a friction fit, at a telescoping region (64). The assembly (10) can be selected from an inventory (300) containing a set of delivery systems (100) of four size aortic section grafts (12) and a set of delivery systems (200) of four size iliac section grafts (14), that together accommodate a large majority of aneurysm sizes, and delivery systems (250) containing four standard sizes of occluders (80).

2 Claims, 11 Drawing Sheets

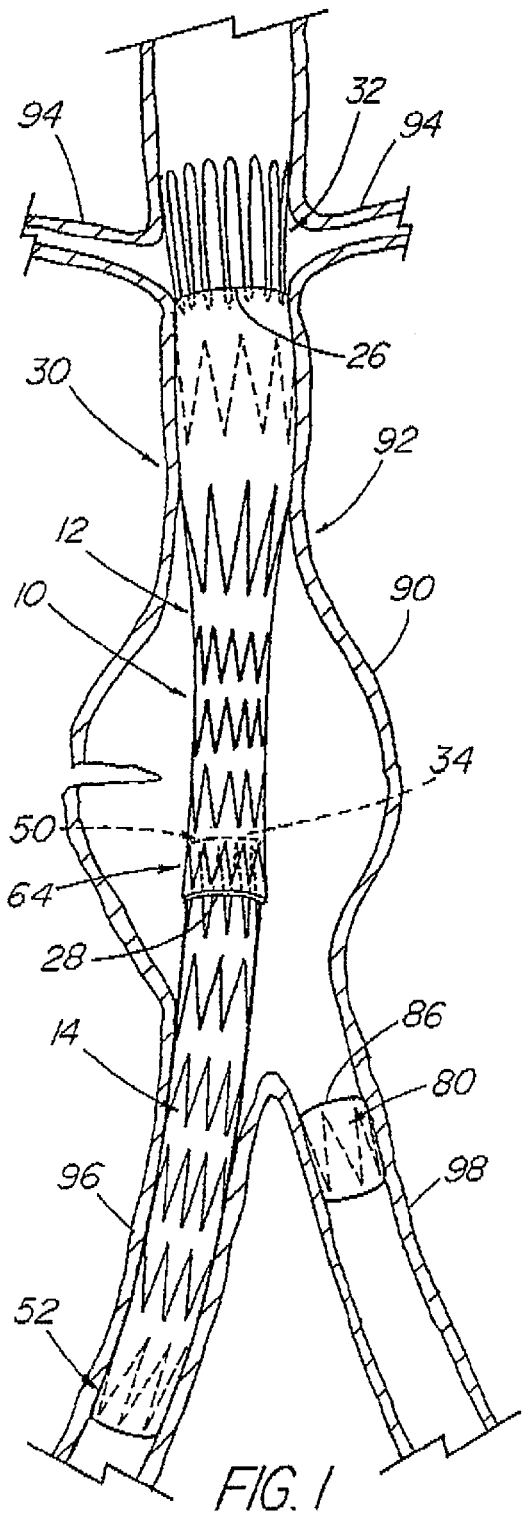
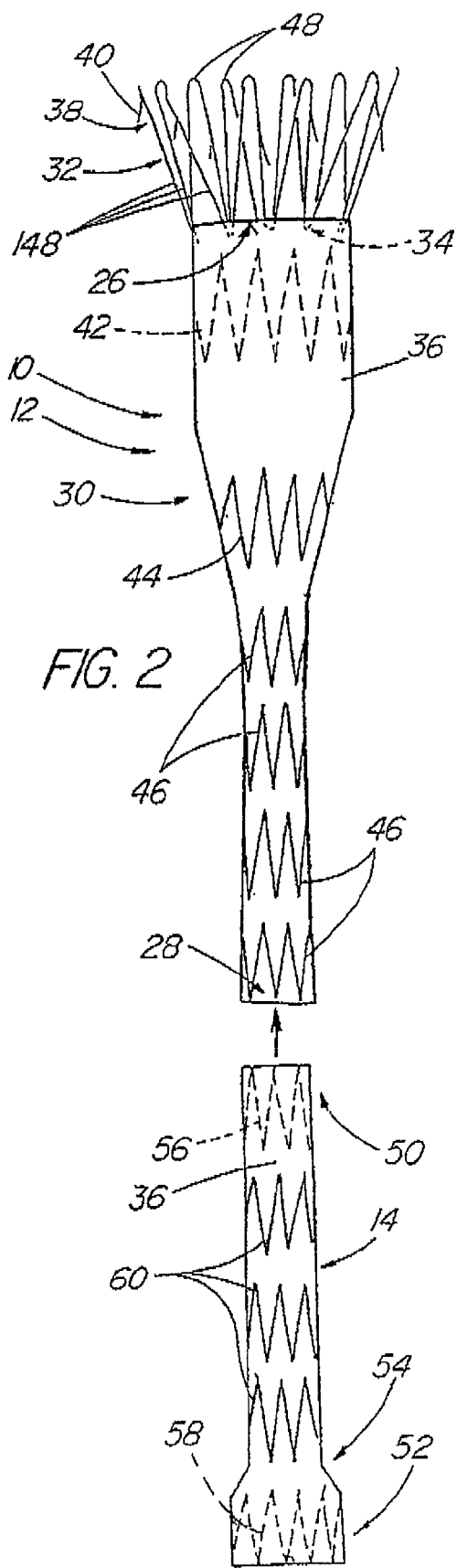
FIG. 1
FIG. 2

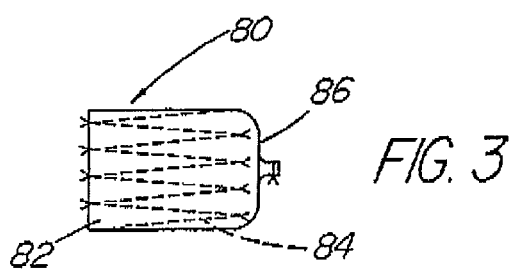
FIG. 3
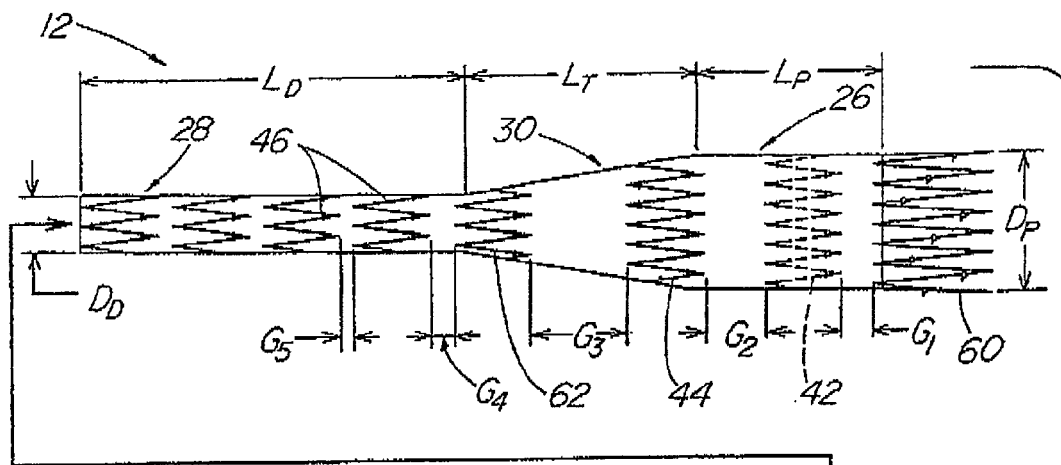
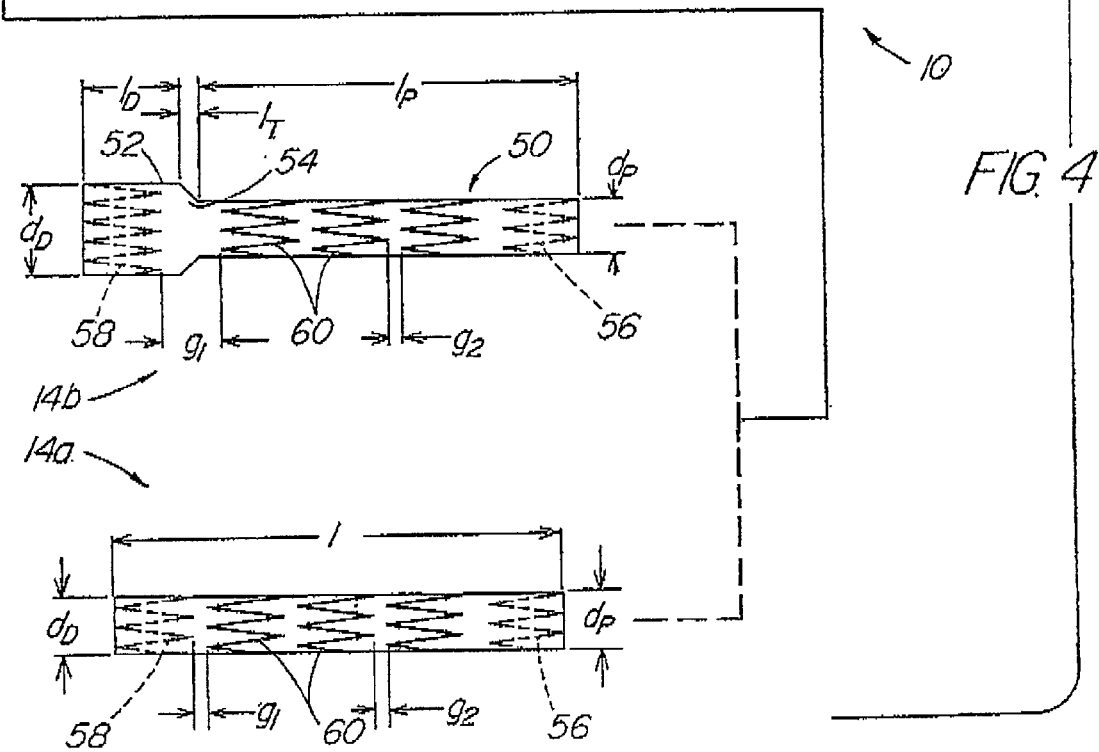
FIG. 4

FIG. 7    DIMENSIONS TABLE

| FIGURE | GRAFT | DIAMETERS (mm) | | | | TOTAL | LENGTHS (mm) | | | | | | INTERSTENT GAP SPACINGS (mm) | | | | | | |
|---|---|---|---|---|---|---|---|---|---|---|---|---|---|---|---|---|---|---|---|
| | | $D_P$ | $d_P$ | $D_D$ | $d_D$ | | $L_P$ | $l_P$ | $L_T$ | $l_T$ | $L_D$ | $l_D$ | $G_1$ | $G_2$ | $G_3$ | $G_4$ | $G_5$ | $g_1$ | $g_2$ |
| FIG. 4 | 12 | 22 26 30 34 | - | 12 | - | 127 | 26 | - | 33 | - | 68 | - | 2 | 5 | 5 | 3 | 3 | - | - |
| | 14a | - | 12 | - | 12 16 20 24 | 94 | - | - | - | - | - | - | - | - | - | - | - | 4 | 3 |
| | 14b | - | 12 | - | 16 20 24 | 94 | - | 73 | - | 4 | - | 17 | - | - | - | - | - | 4 | 3 |
| FIG. 5 | 12 | 22 26 30 34 | - | 12 | - | 122 | 35 | - | 17 | - | 70 | - | 2 | - | - | 5 | 3 | - | - |
| | 12 | 22 26 30 34 | - | 12 | - | 108 | 28 | - | 20 | - | 60 | - | 2 | 14 | - | 3 | 1 | - | - |
| FIG. 6 | 14a | - | 12 | - | 12 16 20 24 | 110 | - | - | - | - | - | - | - | - | - | - | - | 3 | 3 |
| | 14b | - | 12 | - | 16 20 | 110 | - | 56 | - | 34 | - | 20 | - | - | - | - | - | 3 | 3 |
| | 14c | - | 12 | - | 24 | 110 | - | 56 | - | 34 | - | 20 | - | - | - | - | - | 3 | 3 |

FIG. 7

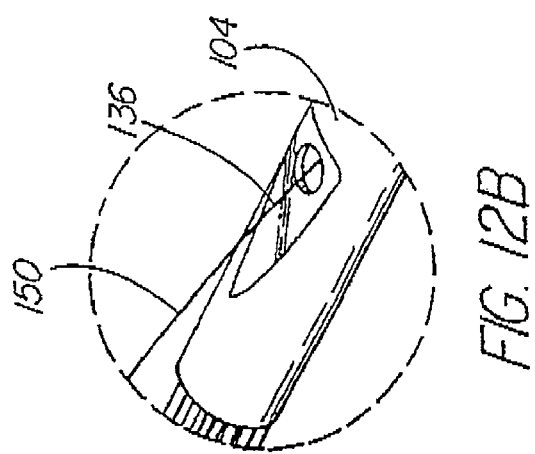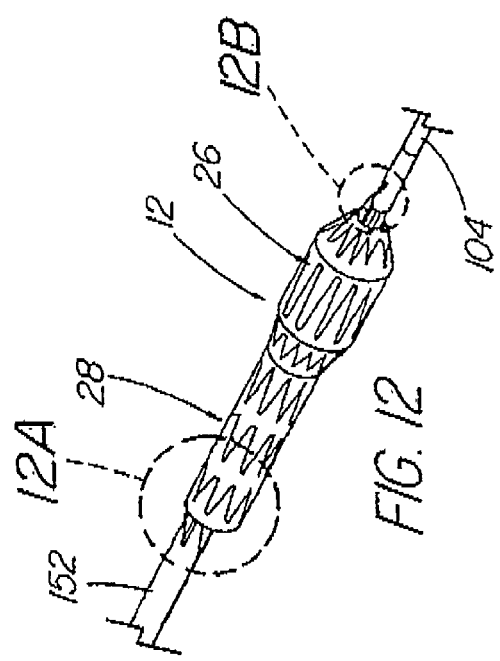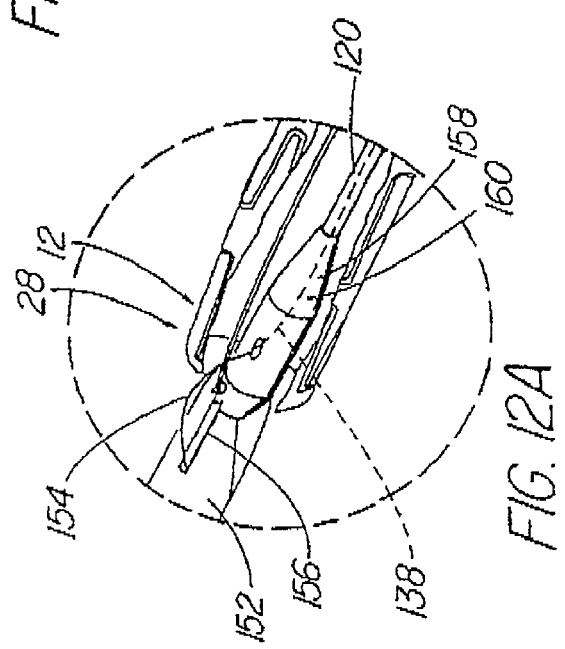

MODULAR STENT GRAFT ASSEMBLY AND USE THEREOF

CROSS-REFERENCE TO RELATED APPLICATIONS

This application claims priority of provisional application Ser. No. 60/279,329, filed Mar. 28, 2001.

TECHNICAL FIELD

The present invention relates to medical devices and more particularly to modular endovascular stent grafts.

BACKGROUND OF THE INVENTION

In recent years treatment of aneurysms has been performed prior to aneurysm rupture and has included the use of stent grafts that are implanted within the vascular system with minimally invasive surgical procedures and that include one or more stents affixed to graft material. The stent grafts are secured at a treatment site by endovascular insertion utilizing introducers and catheters, whereafter they are enlarged radially and remain in place by self-attachment to the vessel wall. In particular, stent grafts are known for use in treating descending thoracic and abdominal aortic aneurysms where the stent graft at one end defines a single lumen for placement within the aorta and at the other end is bifurcated to define two lumens, for extending into the branch arteries.

One example of such a stent graft is disclosed in PCT Publication No. WO 98/53761 in which the stent graft includes a sleeve or tube of biocompatible graft material such as Dacron™ polyester fabric (trademark of E. I. DuPont de Nemours and Co.) or polytetrafluoroethylene defining a lumen, and further includes several stents secured therealong, with the stent graft spanning the aneurysm extending along the aorta proximally from the two iliac arteries; the reference also discloses the manner of deploying the stent graft in the patient utilizing an introducer assembly. The graft material-covered portion of the single-lumen proximal end of the stent graft bears against the wall of the aorta above the aneurysm to seal the aneurysm at a location that is spaced distally of the entrances to the renal arteries. Thin wire struts of a proximal stent extension traverse the renal artery entrances without occluding them, since no graft material is utilized along the proximal stent while securing the stent graft in position within the aorta when the stent self-expands. An extension is affixed to one of the legs of the stent graft to extend along a respective iliac artery and, optionally, extensions may be affixed to both legs. Another known stent graft is the Zenith AAA stent graft sold by William A. Cook Australia Pty. Ltd., Brisbane, Queensland, AU.

Because of life threatening time constraints, such conventional stent grafts are not practical to be utilized with ruptured aneurysms, which presently must be treated, if at all, by open surgery.

Despite the multitude of advances in surgical management and intensive care, the devastating physiological effects of emergency aortic surgery for either ruptured abdominal aortic aneurysms (RAAA) or symptomatic abdominal aortic aneurysms (SAAA), carry an unacceptably high morbidity and mortality rate. Most patients who suffer from RAAA and SAAA are typically unaware of their aneurysmal disease prior to the development of symptoms of actual or impending rupture. The acuity of an RAAA precludes complex radiographic evaluation, does not allow for adequate preoperative planning, and is compounded by the relative unavailability of endovascular stent grafts. Additionally, because of the rapid blood loss from the patient, any substantial surgical delay cannot be tolerated. Another complication stems from the statistical fact that most patients who suffer RAAA or SAAA are elderly and have factors that preclude repair of the rupture by open surgery, with the result that patient mortality from RAAA is very high. Approximately 15,000 deaths per year occur in the United States from ruptured abdominal aortic aneurysms.

Conventional surgical repair of ruptured and symptomatic aneurysms is itself associated with significant complications. Cardiopulmonary complications as a result of a prolonged abdominal operation, significant blood loss and aortic cross clamping, multiple blood transfusions, and hypothermia are most frequently encountered. Mortality of ruptured aneurysms is currently estimated to be between 50% and 75%.

It is thus desired to provide medical devices enabling emergency endovascular treatment of RAAA and SAAA. It is further desired to provide such devices in a manner not requiring, on site at a surgical treatment center, a large inventory of different size devices while still enabling immediate treatment of a large range of aneurysm sizes, nor in a manner requiring preoperative study of the treatment site taking a substantial length of time in order to optimize the selection of an appropriate device. It is yet further desired to provide a medical device that is quickly deliverable and effectively deployable at the treatment site.

SUMMARY OF THE PRESENT INVENTION

The foregoing problems are solved and a technical advance is achieved in an illustrative modular stent graft assembly of the present invention. The stent graft assembly is to be a life-saving device first, and a permanent implant second. Each stent graft assembly comprises at least two components or sections, thus allowing for quick deployment; extensions can be added if necessary. The cranial or aortic section has a diameter corresponding to the normal or undiseased diameter of the aorta of the patient, and the caudal or iliac section has a diameter corresponding to the normal or undiseased diameter of the common iliac artery. The diameter of the aortic section of the assembly is sized to be at least 10 percent larger than the aortic artery for leakproof engagement therewith, while the diameter of the iliac section of the assembly is sized to be at least about 10 percent larger than the ipsilateral iliac artery, both thus assuring no deficiency in diameter that could otherwise result in leakage around the assembly or migration of the assembly following placement. Preferably, each section has an assembly interconnection portion with a constant diameter of, for example, 12 mm for at least a predetermined length of, for example about 56 mm to facilitate interconnection in a wide range of overall assembly lengths. The overall length of the implanted stent graft assembly is adjustable intraoperatively by varying the amount of overlap at the interconnection. An iliac occluder can also be utilized for occluding the contralateral iliac artery, with a conventional crossover connection to be made between the ipsilateral and contralateral iliac arteries, if possible.

A preferred inventory of components or devices includes a set of aortic assembly sections of a common length (exclusive of the attachment stent length) with proximal end portions having one of a standard set (four) of proximal diameters (34, 30, 26 and 22 mm); and iliac sections of a common length with distal end portions having one of a standard set (four) of different distal diameters (24, 20, 16 and 12 mm). In addition, occluders having one of a standard set (four) of different diameters (24, 20, 16 and 14 mm) could be included in the inventory. Such inventory provides for the largest coverage of the different patient anatomy with the fewest number of components or devices; however, the lengths of the assembled devices can be varied to accommodate different patient anatomy.

This invention is designed to perform a compromise operation which can be performed with a maximum of safety and yet produce a satisfactory and safe result. No time is spent on accurately measuring the dimensions of a patient's aorta, and no time is spent on manipulating a second graft down a second iliac artery and to thereby connect a second iliac leg thereto.

The method of use includes inserting the aortic section of the assembly into the aortic artery and engaging the proximal end with portion thereof the aorta just below the renals with the distal end portion extending distally into the aorta. The iliac section is inserted into the ipsilateral artery with engagement thereagainst at the distal end portion thereof. The proximal end portion of the iliac section interconnects with the distal end portion of the aortic assembly section to provide an overlapping interconnection that can be adjusted to accommodate the patient's anatomy. An occluder is then implanted in the contralateral iliac to isolate the ruptured aneurysm.

When an elderly patient is suffering from a rupture or dissection of an aortic aneurysm, all of the blood is immediately bypassed to one of the iliac arteries such as the ipsilateral iliac artery and the patient's life is saved. The provision of the contrailiac occluder and the bypass graft between the contrailiac artery and the ipsilateral iliac artery is a relatively unimportant detail and not too relevant to the life of the patient. Furthermore, the latter detail can be attended to after the ruptured vessel is isolated. The above operation may seem to be somewhat crude, but it is designed to protect the lives of elderly and very ill patients who would otherwise die. Each of the above steps has been performed separately for various reasons, but this is the first time that they have all been performed in sequence in a single permanent operation. One would not be expected to perform such an operation in a single procedure since it seems impractical and clumsy and yet it works and saves lives.

BRIEF DESCRIPTION OF THE DRAWINGS

An embodiment of the present invention will now be described by way of example with reference to the accompanying drawings, in which:

FIG. 1 diagrammatically illustrates the stent graft assembly of the present invention deployed within a ruptured aneurysm, and an occluder in a selected iliac artery;

FIG. 2 is an exploded side view of the stent graft assembly of the present invention having an aortic section and an iliac section;

FIG. 3 shows an occluder plug to be used with the present invention;

FIG. 4 shows a first embodiment of a set of stent graft assembly components having an aortic section graft and two iliac section grafts;

FIG. 7 is a Dimension Table containing dimension information on the stent graft sections of FIGS. 4 to 6;

FIGS. 12, 12A and 12B show enlargements of the trigger wire containment arrangement for the attachment stent (proximal end) and for the distal end portion of the aortic graft;

DETAILED DESCRIPTION

Figure 5:
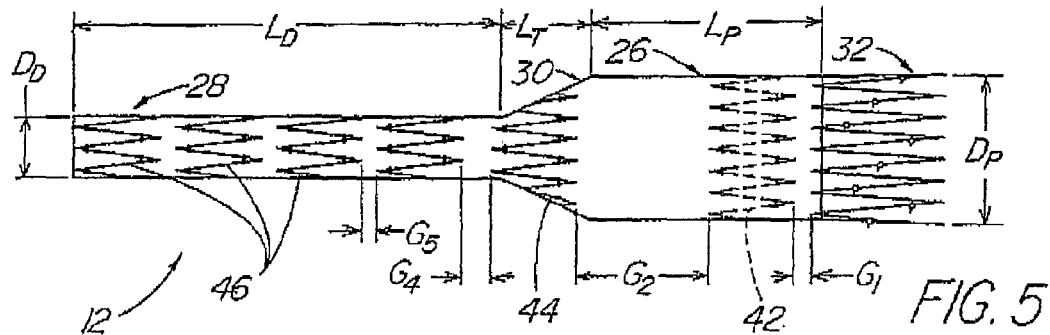
FIG. 5 illustrates a second embodiment of aortic section grafts.

The modular stent graft assembly of the present invention includes one or more devices and is intended for use in the abdominal aorta for symptomatic or ruptured aneurysm repair. Referring first to FIGS. 1 to 3, the stent graft assembly 10 is modular and comprises an aortic section 12, an iliac section 14, and a contralateral iliac occluder 80. Aortic section 12 and iliac section 14 are interconnected and overlap each other within the aneurysm 90 upon deployment, while occluder 80 is deployed separately within the contralateral iliac artery 98. Aortic section 12 is affixed at the aneurysm neck 92 below the renal arteries 94, with iliac section 14 extending into ipsilateral iliac artery 96. A conventional femoro-femoral bypass or cross-over procedure using a bypass graft (not shown) will reconnect the ipsilateral iliac artery to the contralateral iliac artery distal to the occluder 80, to convey blood from the side receiving the entire aortic blood flow through the stern graft assembly, to the other limb, in a manner disclosed in U.S. Pat. No. 5,693,084. The delivery systems (see FIGS. 8 to 11) for each component of the stent graft assembly are each comprised of a sheath into which the stent graft (or plug) is compressed, and a tapered tip for a smooth transition from wireguide-to-sheath diameters. The delivery system for the aortic section uses trigger wire release mechanisms to lock the endovascular graft onto the delivery system until the graft is precisely positioned axially and then released by the physician to be deployed at the deployment site. The delivery system is compatible with an 0.035 in (0.889 mm) wire guide.

The aortic section 12 includes a proximal end portion 26 and a distal end portion 28, with a tapered transition portion 30 that interconnects the distal end portion having a constant diameter of 12 mm, and the proximal end portion 26 having a selected larger diameter. An attachment stent 32 is secured to the proximal end portion, with the stent's distal end portion 34 along the inside surface of the graft material 36, while the remaining attachment portion 38 extending proximally from the graft material and having barbs 40 for example for becoming affixed to the vessel walls. Aortic section 12 also has several additional stents 42,44,46 with stent 42 adjacent to the attachment stent being disposed within the graft material, and stents 44,46 being secured about the outer surface of the graft material 36 along the length thereof distally of the attachment stent 32 and stent 42. The proximal end portion 26 preferably is denoted by a plurality of radiopaque markers (not shown) such as gold marker members for facilitating fluoroscopic visualization of the proximal end of the graft material, for placement distally of the renal arteries.

The contralateral iliac artery occluder in FIGS. 1 and 3, may be a conventional occluder 80, such as the Zenith AAA™ Iliac Plug sold by William A. Cook Australia Pty. Ltd., Brisbane, Queensland, AU, which comprises a tubular length of graft material 82 of 20 mm with a single stent 84 sutured therewithin, having a diameter of between about 14 mm and 24 mm; one end 86 of the tubular structure traverses and closes the lumen therethrough with graft material 82 for sealing. A procedure for delivering such a contralateral iliac occluder and for performing a femoro-femoral bypass or cross-over procedure using a bypass graft, is disclosed in U.S. Pat. No. 5,693,084.

Preferably, the present invention includes a set of graft components limited in number but selected to accommodate most rupture sites, and includes four aortic sections 12 each differing in the size of their proximal diameters, and includes four iliac section 14 each differing in the size of their distal diameters, while the diameters of the distal ends of the four aortic sections 12 and the diameters of the proximal ends of the four iliac sections 14 is constant among the eight bodies. Preferably, the proximal diameter of the aortic section 12 is standardized for each of four aortic sections to have one of four dimensions: 34 mm, 30 mm, 26 mm and 22 mm. The distal end portion 52 of the iliac section 14 is standardized for each of four iliac sections to have one of four standardized diameters: 24, 20, 16 and 12 mm.

Figure 6:
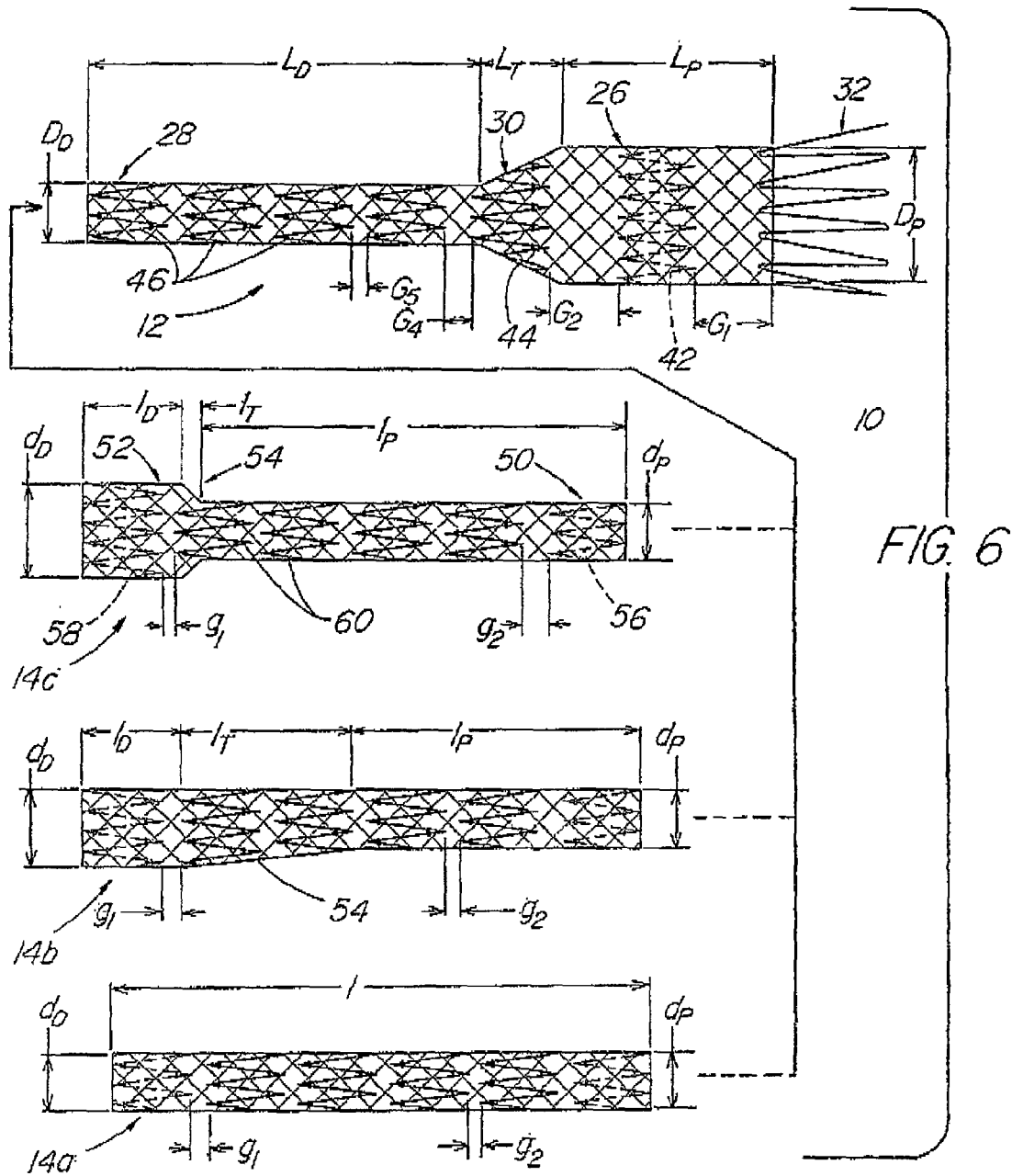
FIG. 6 shows a third embodiment of a set of graft assembly components having an aortic section style and three iliac graft styles.

Several designs or embodiments of aortic sections are shown in FIGS. 4 to 6, and several designs or embodiments of iliac sections are also shown in FIGS. 4 and 6. Dimension information for the different standard sizes for the designs of the tubular grafts in FIGS. 4 to 6 is contained in the Dimension Table, FIG. 7, for easy reference, and includes proximal end and distal end diameters; proximal, distal and transition portion lengths; and interstent gap spacing for both the aortic and iliac tubular grafts. The lengths of the stents and their geometries and spacing can be varied to increase or decrease the flexibility of the system; also, two stents could optionally be utilized in the proximal end portion of the aortic section tubular graft.

With respect to FIG. 4, one aortic section tubular graft 12 is shown, and two designs of iliac section tubular grafts 14a, 14b are shown. The diameter $D_P$ of the proximal end of aortic tubular graft 12 is one of four standardized diameters: 34 mm, 30 mm, 26 mm and 22 mm. The diameter $D_D$ of the distal end is 12 mm. The total length is preferably about 127 mm, with the proximal end portion length $L_P$ being 26 mm; the transition portion length $L_T$ being 33 mm; and with the distal end portion length $L_D$ being 68 mm. Transition portion 30 is shown to include two transition stents 44, 62 with substantial spacing therebetween. Regarding interstent gap spacings, $G_1$ between the attachment stent and the first stent 42 is 2 mm; $G_2$ between first stent 42 and first transition stent 44 is 5 mm; $G_3$ between the first and second transition stents 44, 62 is 5 mm; $G_4$ second transition stent 62 and the adjacent distal stent 46 is 3 mm; while gaps $G_5$ between the several distal stents 46 are 3 mm.

The iliac section tubular graft 14a has a proximal end portion 50 with a diameter $d_P$ of 12 mm, and a distal end portion 52 of a selected diameter $d_D$ of also 12 mm. Also, preferably, iliac tubular graft 14a has a total length of 94 mm, with the proximal end portion length $I_P$ being about 73 mm in length, the distal end portion length $I_D$ being about 17 mm in length, and there is no tapered transition portion extending between the proximal and distal portions since the proximal and distal diameters are the same. As to iliac section tubular graft 14b, also having a total length of 94 mm, the diameter $d_P$ is 12 mm while the distal end portion has a selected diameter $d_D$ of 16, 20 or 24 mm. Proximal end portion length $I_P$ is 73 mm; transition portion 54 has a length $I_T$ of 4 mm; and distal end portion length $I_T$ is 17 mm. The proximal and distal end portions may have respectively a proximal-most and a distal-most stent 56,58 affixed internally of the graft material, and three axially short stents 60 therebetween affixed externally of the graft material 36. Gap $g_1$ between distal stent 58 and the adjacent stent 60 is 4 mm, while gaps $g_2$ between the remaining stents 56,60 are 3 mm.

Referring now to FIG. 5, the proximal end portion 26 of the aortic section tubular graft 12 has a length $L_P$ of about 35 mm with one stent 42 therewithin, the distal end portion 28 has a length $L_D$ of about 70 mm with four axially short stents 46 therearound, and the tapered transition portion 30 therebetween has a length $L_T$ of about 17 mm with one transition stent 44 therearound. Transition portion 30 is seen to have only one transition stent 44 therearound and is shorter than the transition portion 30 of the embodiment of FIG. 4. Regarding interstent gap spacings, $G_1$ between the attachment stent and the first stent 42 is 2 mm; $G_2$ between first stent 42 and transition stent 44 is 14 mm; $G_4$ between transition stent 44 and the adjacent distal stent 46 is 5 mm; while gaps $G_5$ between the several distal stents 46 are 3 mm. The iliac section tubular grafts for use therewith may be identical in design and dimension to those shown in FIG. 4.

In FIG. 6 is shown one aortic section tubular graft 12, and three designs of iliac section tubular grafts 14a,14b,14c. The total length of the aortic tubular graft 12 and each of the iliac tubular grafts is about equal. The diameter $D_P$ of the proximal end of aortic tubular graft 12 is, again, one of four standardized diameters: 34 mm, 30 mm, 26 mm and 22 mm. The diameter $D_D$ of the distal end is 12 mm. The total length is preferably about 108 mm, with the proximal end portion length $L_P$ being 28 mm; the transition portion length $L_T$ being 20 mm; and with the distal end portion length $L_D$ being 60 mm. Regarding interstent gap spacings, $G_1$ between the attachment stent and the first stent 42 is 2 mm; $G_2$ between first stent 42 and transition stent 44 is 3 mm; $G_4$ between transition stent 44 and the adjacent distal stent 46 is 3 mm; while gaps $G_5$ between the several distal stents 46 are 1 mm.

As with the iliac section tubular grafts of FIG. 4, the proximal and distal end portions of iliac tubular grafts 14a,14b,14c of FIG. 6 have respectively a proximal-most and a distal-most stent 56,58 affixed internally of the graft material, and four axially short stents 60 therebetween affixed externally of the graft material 36. The iliac tubular graft 14a has a proximal end portion 50 with a diameter $d_P$ of 12 mm, and a distal end portion 52 of a selected diameter $d_D$ of also 12 mm. Also, preferably, iliac tubular graft 14a has a total length of 110 mm, and there is no tapered transition portion extending between the proximal and distal portions since the diameters are the same. As to iliac tubular graft 14b, also having a total length of 110 mm, the diameter $d_P$ is 12 mm while the distal end portion has a selected diameter $d_D$ of 16 or 20 mm. Proximal end portion 50 length $I_P$ is 56 mm; transition portion 54 has a length $I_T$ of 34 mm; and distal end portion 52 length $I_D$ is 20 mm. Gap $g_1$ between distal stent 58 and the adjacent stent 60 is 3 mm, and gaps $g_2$ between the remaining stents 56,60 are also 3 mm. Iliac section tubular graft 14b differs from graft 14c in that graft 14C has a distal diameter of 24 mm. The transition portion need not be precisely symmetrically tapered, as can be seen.

Regarding the differences between the embodiments of FIGS. 4, 5 and 6, the transition portion of the aortic section graft 12 of FIG. 4 is elongated with two stents therearound spaced substantially from each other, in comparison with the transition portions of the aortic grafts of FIGS. 5 and 6. The greater spacing provides more flexibility while utilizing two stents minimizes any tendency of the graft to buckle and close slightly, when finally deployed in the aneurysm and also thereafter as the aneurysm shrinks over time, and minimizes the chance of endoleaks. The longer, more gradual taper of the transition portion of FIG. 4 reduces somewhat forces from the blood flow through the deployed stent graft assembly tending to pull the stent graft assembly distally, and thus reduces any tendency of the graft assembly to migrate. Turbulent blood flow is also further reduced with the longer transition portion because of the longer transition portion length. The aortic section graft 12 of FIG. 4 has a longer total length than the lengths of aortic grafts 12 of FIGS. 5 and 6, while the iliac section grafts are correspondingly shorter with one less stent therealong, and with a shorter transition portion having no stent therearound.

The graft to be selected is based on the findings from preoperative radiologic studies, including computerized tomography (CT), magnetic resonance imaging (MRI), or conventional angiography. The outside diameter of the graft is intended to be at least 10 percent larger than the proximal implantation site. The attachment site for distal implantation is also oversized at least about 10 percent. The assumption is being made that a small amount of graft redundancy or vessel stretching would be inconsequential, whereas a small deficiency in the diameter of the graft could result in either endoleakage or migration. Determination of the proximal diameter of the aortic graft depends primarily on a measurement of the aneurysm neck 92 from preoperative or intraoperative imaging. If the neck of the aneurysm 90 appears to have an elliptical section on trans-axial images, the true profile is assumed to be circular and the true diameter is the diameter of the narrowest part of the ellipse. If CT scanning is unavailable, intraoperative intravascular ultrasound (IVUS) may be used to determine the diameter. In determining the graft length, the intended implantation sites must first be identified. The proximal implantation site is generally just distal to the lowest renal artery 94 so that the graft material 36 does not cover the renal arteries 94, with attachment made by the proximal bare stent portion 38 extending over and past the renal arteries. The distal implantation site is in the ipsilateral iliac artery 96 (typically proximal to the takeoff of the hypogastric artery). Both sections of the stent graft assembly have fixed lengths. The overall length of the assembly is adjusted intraoperatively by varying the amount of overlap at the interconnection of the two sections.

Figure 8:
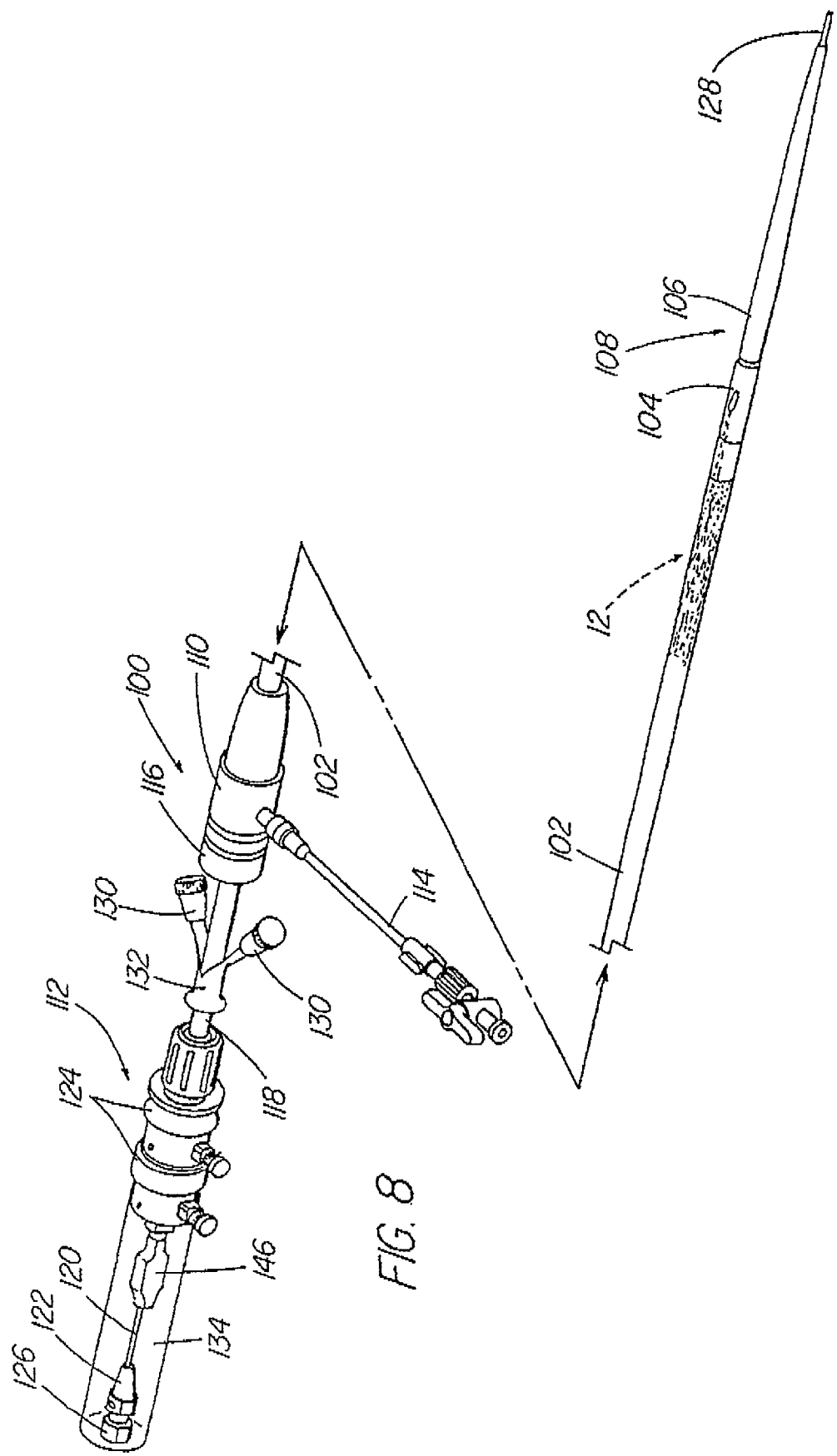
FIGS. 8 to 11 show the delivery systems for the three components, with FIG. 9 showing the trigger wire controls included in the aortic section system of FIG. 8.
Figure 9:
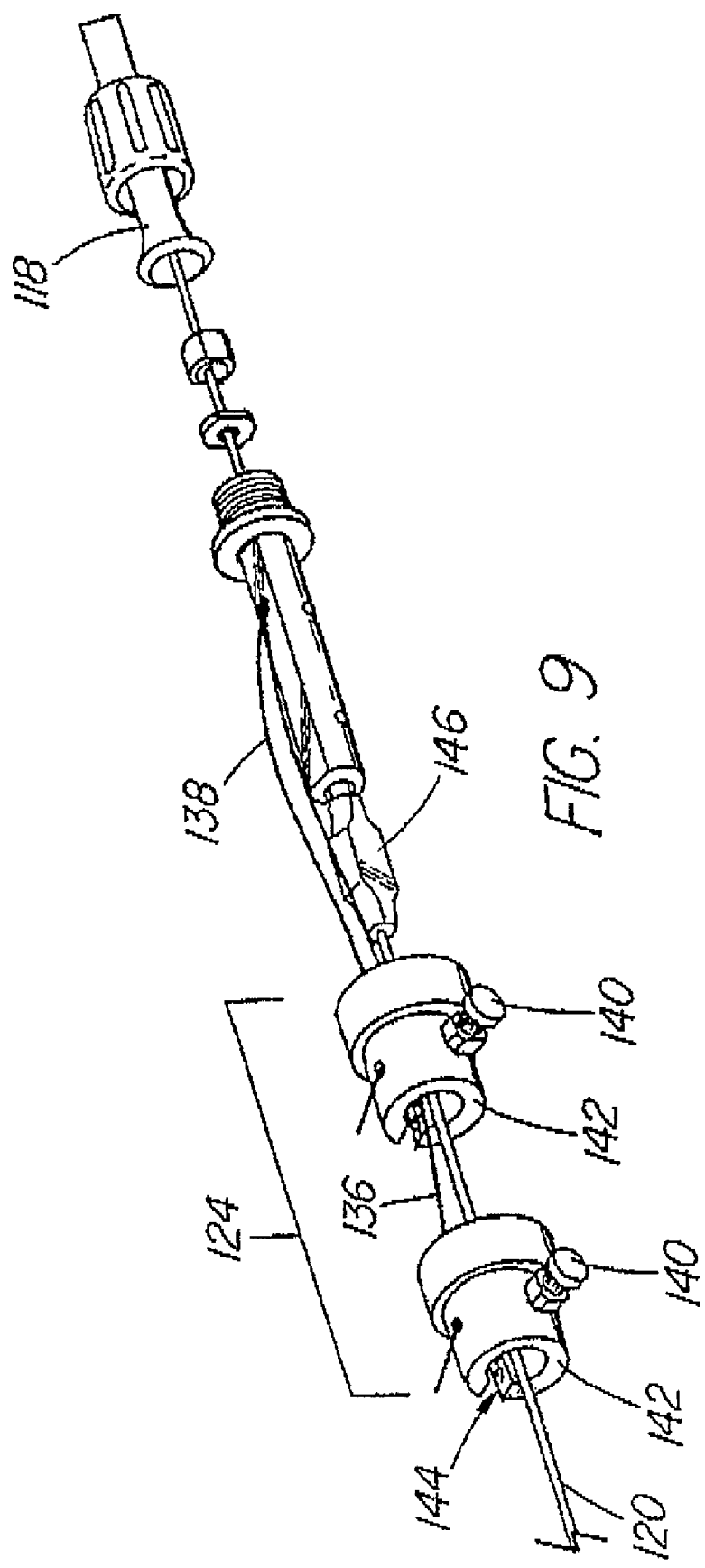

Referring to FIGS. 8 to 11, the delivery systems for the aortic section, iliac section and contralateral iliac occluder will now be described. The delivery system 100 for aortic sections 12 is illustrated in FIGS. 8 and 9, having a delivery sheath 102, a top cap 104 and tapered dilator 106 at proximal end 108, and a fitting 110 at distal end 112 of the delivery system. Top cap 104 is affixed to the distal end of dilator 106, which is affixed at the proximal end of a small diameter inner cannula 120 that extends completely through the delivery system to the distal end. Fitting 110 is affixed to sheath 102, and joined to the side of fitting 110 is injection system 114, for saturating the stent graft with anticoagulant heparin prior to deployment, and optionally for the injection of contrast medium thereafter. At the distal end of fitting 110 is a check-flow valve 116 through which extends pusher 118. Distally of pusher 118 is seen handle 122 of cannula 120, and trigger wire control systems 124.

Stylet 126 extends through cannula 120, through pusher 118 and introducer sheath 102 and top cap 104 to a proximal tip 128 that protrudes from the proximal end of the tapered dilator 106; stylet 126 is of protective value during shipping and handling but is removed prior to use in the medical procedure. Tabs 130 are provided at the distal end of short sheath 132, for peeling away the sheath prior to the medical procedure; sheath 132 protects the patency of the introducer lumen at the check-flow valve during shipping and handling, and extends only into fitting 110. For protection of the distal end components during handling, a protective tube 134 is secured therearound, and it also is removed prior to the procedure.

Trigger wire control systems 124 are shown in greater detail in FIG. 9. Control systems 124 for the two trigger wires 136,138 of the delivery system 100 each include a safety lock 140 that is removed laterally, and a release ring 142 that is moved distally (away from the patient) parallel to the cannula 120 and pulls the respective trigger wire out of the assembly. The trigger wire 136 for securing the attachment stent 32 of the aortic graft 12 against any axial movement until released, is first to be removed prior to being able to actuate the controls for trigger wire 138 that secures the distal end portion 28 of the aortic graft against any axial movement until released. Also, the release ring 142 for the distal end portion may be a different color than that for the attachment stent, to clearly indicate to the physician which trigger wire the particular control system actuates. The release rings 142 have axial slots 144 therealong to permit lateral removal from about the inner cannula 120. Pin vise 146 tightens upon and releases inner cannula 120 so that top cap 104 and tip 106 can be advanced to deploy and be withdrawn for docking and system withdrawal.

Figure 10:
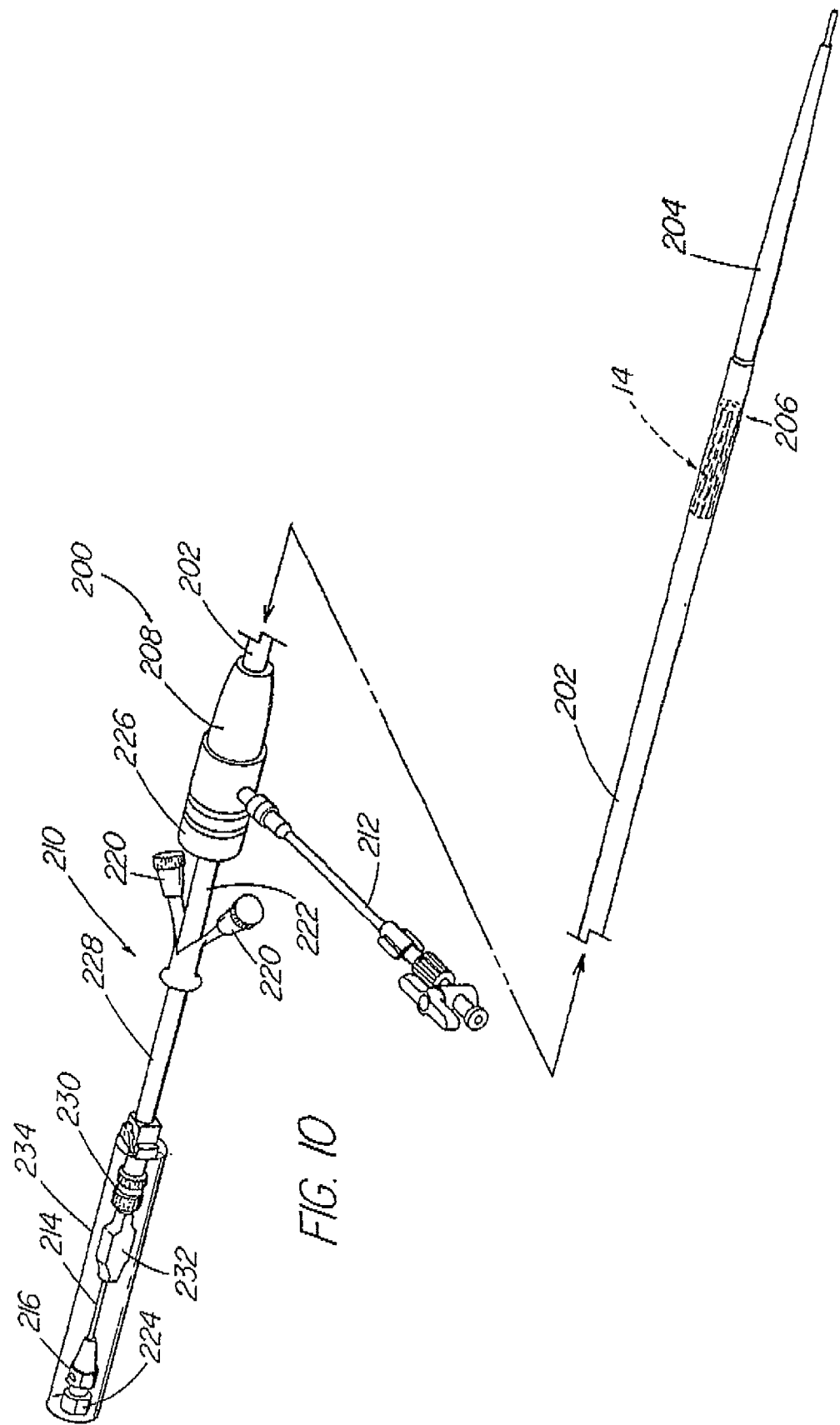

Delivery system 200 for extension leg 14 is shown in FIG. 10, and is similar to system 100, including a delivery sheath 202, tapered dilator 204 at proximal end 206, and a fitting 208 at distal end 210 of the delivery system. Joined to the side of fitting 208 is the heparin injection system 212, and inner cannula 214 with handle 216 therefor extends from distal end 210. Tabs 220 are provided at the distal end of short sheath 222 that extends only into fitting 208, for peeling away the sheath prior to use, and stylet 224 is also removed prior to use. Also in FIG. 10 is seen check-flow valve 226, pusher 228, pusher fitting 230 and pin vise 232, with a protective tube 234 thereover similar to protective tube 134 of FIG. 7.

Figure 11:
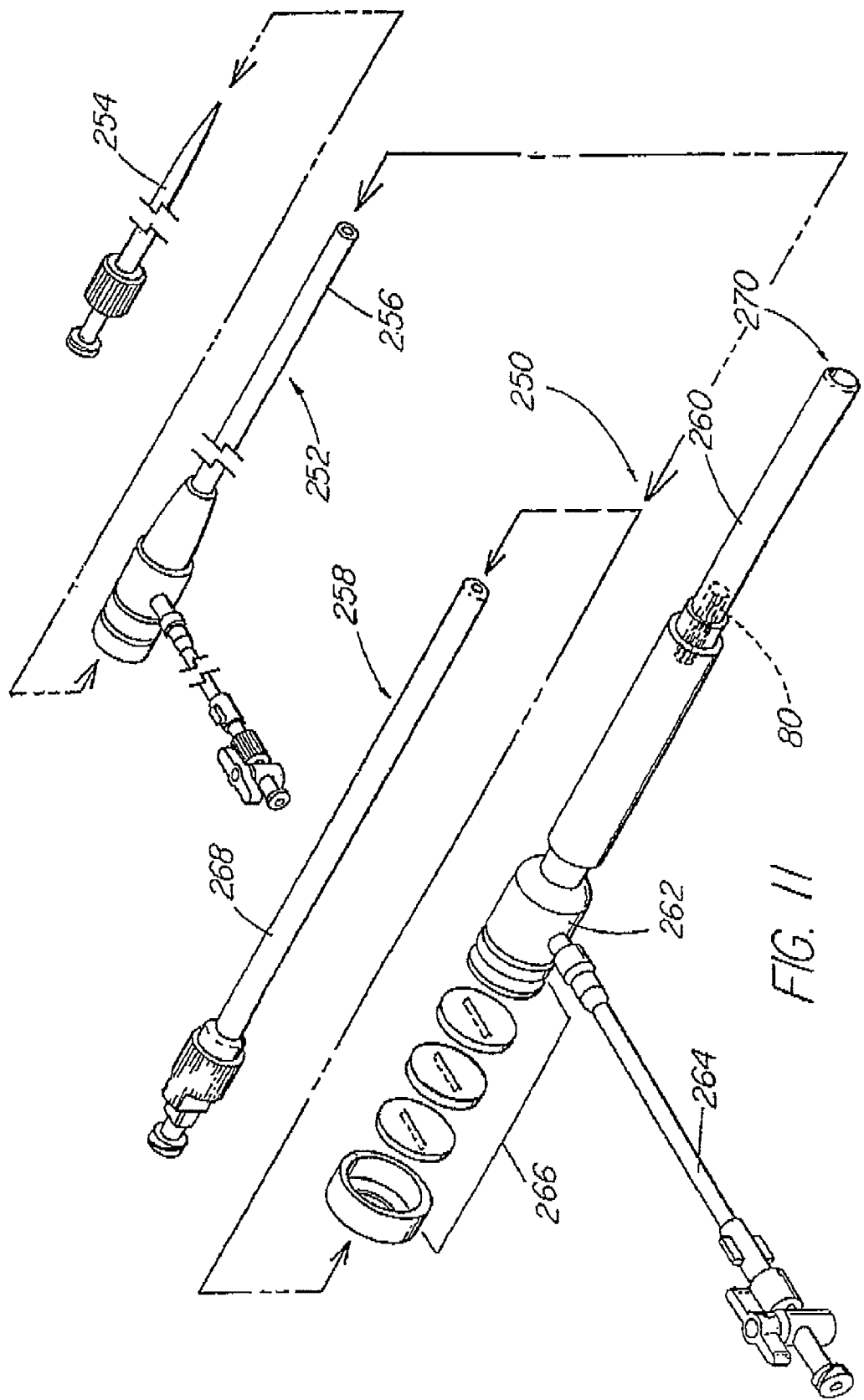

Delivery system 250 for a conventional contralateral iliac occluder 80 is shown in FIG. 11, and includes two assemblies. Introducer 252 includes a tapered dilator 254 and a delivery sheath 256 that is adapted for delivery over a guide wire along the contralateral iliac artery. Second assembly 258 includes a short sheath 260 containing occluder 80, a fitting 262 with a heparin injection system 264 extending from the side thereof, a three-disk check-flow valve 266, and a pusher 268 for pushing the contralateral iliac occluder 80 from the distal end of the sheath 260. Proximal end 270 of sheath 260 is inserted into the proximal end 272 of introducer 252 once the introducer is positioned and the guide wire and dilator removed. Pusher 268 then is utilized to move the occluder 80 into the delivery sheath 256 and therealong to the deployment site adjacent to the bifurcation with the aorta. Alternatively, an occluder may be utilized that is deliverable over a guide wire, and that transversely closes completely upon withdrawal of the guide wire after complete deployment of the occluder.

Figure 14:
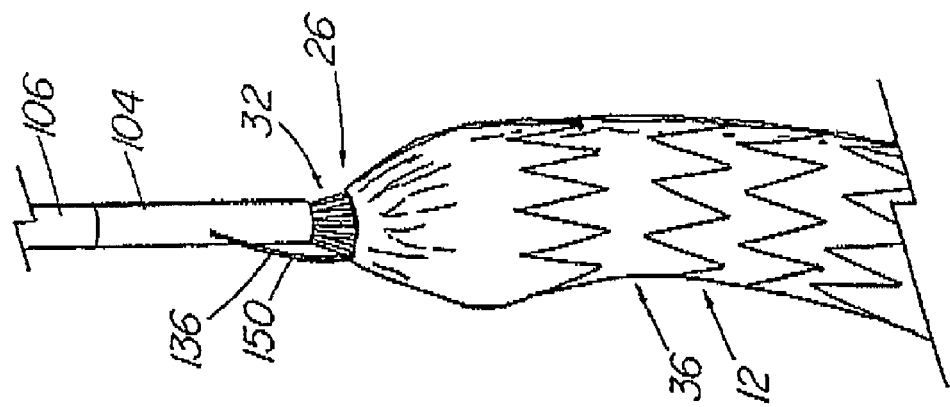
FIGS. 13 and 14 are enlargements of the proximal end of the aortic graft showing the trigger wire locking mechanism for the attachment stent.
Figure 13:
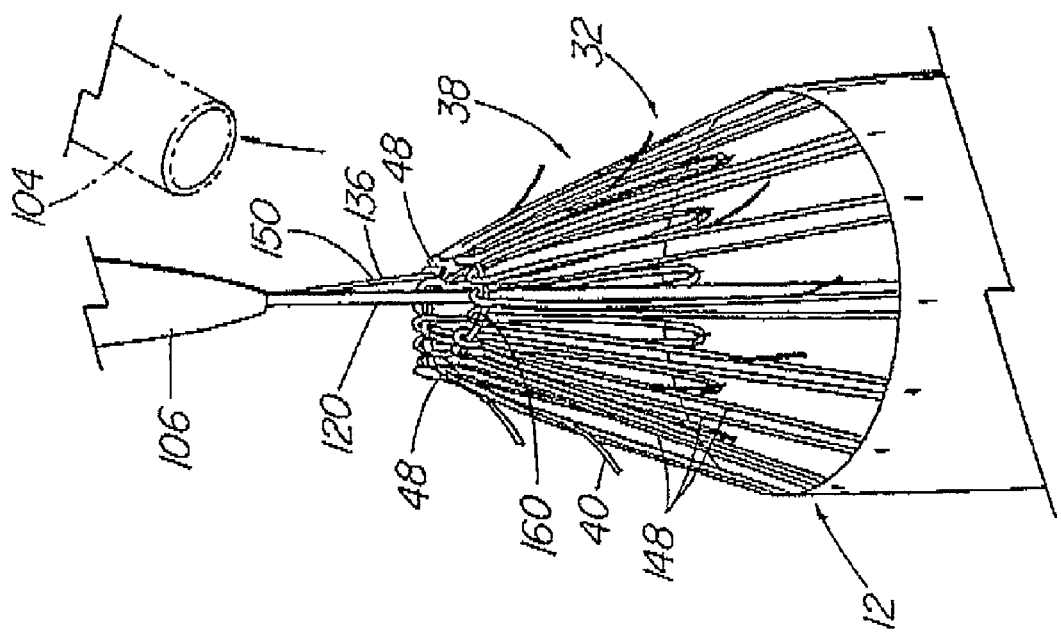

In FIGS. 12 to 14, the trigger wire 136 is shown in detail in relationship to attachment stent 32 of aortic graft 12. FIG. 13 illustrates attachment stent 32 before top cap 104 has been placed over the exposed struts 148, during which a suture holds the strut ends 48 gathered near the inner cannula 120; the suture is removed once the top cap is in place. Trigger wire 136 extends from its control section 124 along small diameter cannula 120 of the delivery system 100 within pusher 118, and includes a locking section 150 that extends outwardly through an aperture of proximal pusher body 152 and forwardly through aortic graft 12 and then outwardly thereof near proximal end 26 thereof, then forwardly and into a small aperture of the top cap and through a loop at the joined proximal ends 48 of a pair of struts 148 and then further into the dilator, held therein by friction fit by the inner cannula threaded into the dilator. Release portion 150 holds the proximal ends 48 of the exposed struts of the attachment stent within the top cap, fixed against axial movement with respect to the top cap and dilator. Top cap 104 surrounds all the exposed struts 148 of attachment stent 32 when the aortic section graft 12 is delivered to the site of the ruptured aneurysm, until it is accurately positioned at the aneurysm neck.

First sheath 102 is then pulled distally with respect to aortic graft 12 by manual movement of fitting 110 while the struts of the attachment stent are held within and still restrained within top cap 104, as seen in FIGS. 12 and 14, after which trigger wire 136 is pulled from the top cap and withdrawn completely from the catheter, thus releasing the loop of the attachment stent struts. With the aortic graft held against axial movement relative to pusher 118 by trigger wire 138, the dilator/topcap/cannula assembly is pushed forwardly (proximally) by pushing forwardly on cannula handle 122 to release the attachment stent 32, whereupon the ends 38 of struts 148 self-expand radially outwardly to engage the vessel wall, as shown in FIG. 1, and barbs 40 seat into the vessel wall to thereafter secure the aortic graft 12 in its desired position. Such a trigger wire system is disclosed in WO 98/53761. Optionally, a molding balloon may be used to inflate within self-expanded attachment stent 32 to assuredly press the struts against the vessel wall and seat the barbs.

Similarly, as shown in FIG. 12A, the second trigger wire 138 secures the distal end portion 28 of aortic graft 12 against any axial movement as the top cap 104 is being urged forwardly from attachment stent 32 which would otherwise tend to pull the attachment stent and the aortic graft due to friction. Trigger wire 138 includes release portion 154 that first extends outwardly from proximal pusher body 152 and along groove 156, then inwardly through the graft material of the distal end portion 28 and through a stent end 48 loop and into an opening in the proximal pusher body 152, and then forwardly along inner cannula 120 where it is held in a force fit thereagainst by the proximal tip of pusher 118. Then, upon actuation of its control system 124, trigger wire 138 is pulled from the delivery system which releases the distal end portion 28 of the aortic graft 12 which then fully self-expands within the aneurysm toward the vessel wall.

Proximal pusher body 152 is then pushed proximally through now-deployed aortic graft 12 to abut against the distal end of the top cap 104; the abutment portion of proximal pusher body 152 is selected to have an outer diameter the same as the distal end of the top cap. The configuration of proximal pusher body 152 is shown in FIG. 12. Upon pulling the dilator/topcap/cannula assembly distally, and in turn upon moving proximal pusher body 152 distally, tapered surfaces of the distal end (not shown) of the proximal pusher body gently engage and deflect radially outwardly any portions of the stents of the aortic graft to prevent any stubbing or snagging that otherwise would occur by engagement of the top cap distal end were it to be exposed when pulled distally through the now-deployed aortic graft 12. Proximal pusher body 152 similarly has tapered surfaces 158 at its proximal end 160 that gently engage and deflect outwardly any stent portions when it is pushed proximally through the aortic graft to abut top cap 104. Delivery system 100 is then removed from the patient.

Then, delivery system 200 is introduced into the patient through sheath 102 and ipsilateral iliac artery 96 and into distal end portion 28 of aortic section 12 that is now deployed in the aneurysm, until the proximal end portion 50 of iliac section 14 is within distal end portion 28. Proximal end portion 50 of iliac section 14 is then released in a fashion similar to aortic section 12 (although no trigger wires or top cap are involved), and self-expands to press against the inner surface of distal end portion 28 in telescoping region 64 and establish a friction fit therewithin, after which distal end 52 of iliac section 14 is then released to self-expand against the vessel wall of ipsilateral iliac artery 96, completing the assembly and deployment of stent graft 10 in the aorta of the patient, with proximal end portion 26 of aortic section sealing against the vessel wall in the aneurysm neck 92, and the distal end portion 52 of iliac section 14 sealing against the vessel wall of the ipsilateral iliac artery.

Delivery system 250 is then delivered through the contralateral iliac artery to deliver the contralateral iliac occluder 80 to its proper location distally of the aortic/iliac bifurcation. Occluder 80 is then pushed as sheath 256 is withdrawn, so that occluder 80 emerges from the sheath proximal end and self-expands to press and seal against the vessel wall of the contralateral iliac artery, whereafter the delivery system 250 is fully withdrawn from the patient. The femoro-femoral bypass graft is then secured to connect the ipsilateral iliac artery to the contralateral iliac artery distally of the occluder.

After deployment of the stent graft 10 and the occluder 80 and securing of the bypass graft, blood will flow into proximal end portion 26 of aortic section tubular graft 12, and through the remainder of stent graft assembly 10 into the ipsilateral iliac artery, completely bypassing the ruptured aneurysm, and a portion of the blood flow will pass through the bypass graft to the contralateral iliac artery.

The deployment systems are fabricated with a single lumen vinyl radiopaque tubing of 18 to 20 Fr (6.0 to 6.67 mm) aortic section or a 14 to 16 Fr (4.66 to 5.33 mm) iliac section, an 18 gauge cannula (stainless steel), 0.013 and 0.015 in (0.330 and 0.381 mm) trigger wires (stainless steel), nylon radiopaque top cap and radiopaque PTFE sheath material. The graft consists of uncrimped tubular fabric such as Twillweave™ Micrel™ polyester fabric (product of Vascutek) with stents such as of stainless steel strategically sewn into place with suture such as braided polyester and monofilament polypropylene suture. The stents are preferably well-known self-expanding Gianturco Z-stents, however, balloon expandable stents an also be used. The stent at the proximal end of the aortic section preferably contains barbs that are placed at a 3 mm stagger. A number of gold marker bands are preferably positioned around the top of the main graft body to facilitate fluoroscopic visualization.

The stent graft aortic section and iliac section delivery system is designed to first be inserted into the femoral artery following surgical exposure of the artery. Prior to the insertion of the delivery system, the ruptured aneurysm is properly diagnosed and controlled if necessary with an occlusion balloon, and access to the artery is achieved with an arterial needle, "J" wire, and appropriate angiographic equipment. The "J" wire is exchanged for a stiff guide wire.

The aortic section is then inserted and deployed as described in the instructions for use. Guide wire access is kept through the aortic section. The iliac section is then placed in a similar fashion to the aortic section and is positioned so that the distal portion will be deployed at the proper implantation site and there is at least one, preferably two, full stent overlap between the iliac section and the aortic section. Access is gained in a similar way to the contralateral femoral artery with a large sheath, and the occluder is then loaded and deployed through the large sheath. The attachment of the stent graft at the implantation site can be maximized by inflating a molding balloon at each site to fully expand the attachment stent to press against the arterial wall and seat the barbs of the stent into the wall.

Figure 15:
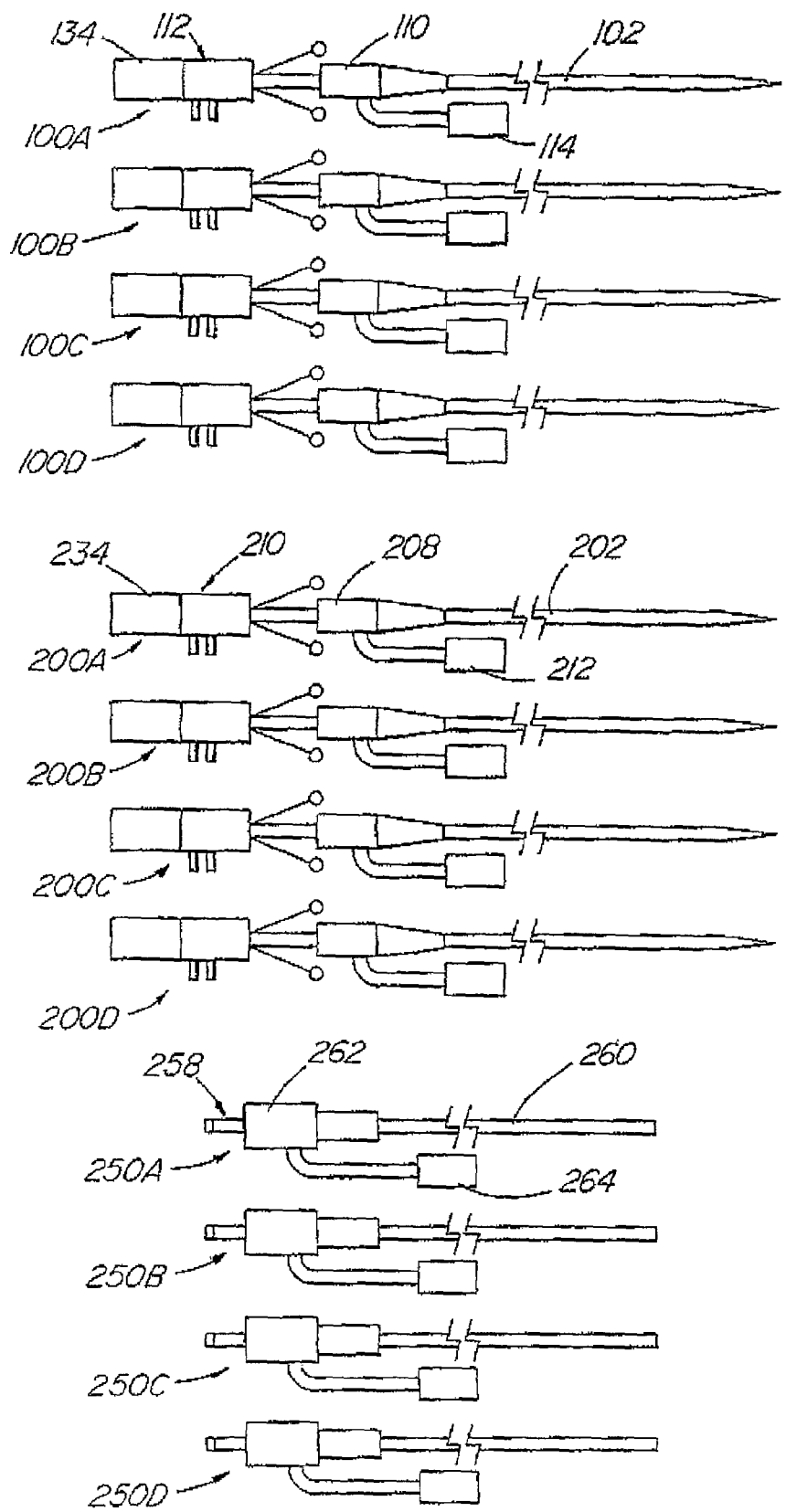
FIG. 15 depicts a complete set of delivery systems having four standard size aortic section grafts, four standard size iliac section grafts, and four standard size occluders.

A complete inventory or set of delivery systems 300 for treatment of a ruptured aneurysm is depicted in FIG. 15. The set 300 includes delivery systems $100_A, 100_B, 100_C, 100_D$ each containing an aortic section graft having a different one of the standardized proximal diameters; delivery systems $200_A, 200_B, 200_C, 200_D$ each containing an iliac section graft having a different one of the standardized distal diameters; and delivery systems $250_A, 250_B, 250_C, 250_D$ each containing an occluder having a different one of the standard diameters for the iliac vessel. The set thus allows the practitioner to quickly select an aortic section graft size and an iliac section graft size and to begin treatment immediately. The set 300 thus provides a minimized inventory of delivery systems capable of treating a great majority of ruptured aneurysms with only relatively rudimentary aneurysm size estimation procedures. Immediate replacement of the delivery systems actually used in a particular treatment, can then be made to complete the set for the next emergency ruptured aneurysm event.

No particular departure is necessary from the usual perioperative management of patients undergoing aneurysm repair. The perioperative evaluation and intraoperative monitoring should be performed as though the patient was undergoing conventional surgical repair. Post-operative management should be dictated by clinical circumstances, and is likely to differ somewhat from the usual management of patients following aneurysm repair, because the patients should tend to experience fewer physiologic difficulties.

What is claimed is:

1. A kit of parts for a modular stent graft assembly for repairing a ruptured or symptomatic aneurysm in an aortic artery, said kit of parts comprising:

a set of aortic sections each having a proximal end portion with a second diameter different from the second diameter of any other proximal end portion of the aortic sections in the set and greater than a first constant diameter of a distal end portion, each aortic section including a first tubular graft having a proximal end portion and a distal end portion, said distal end portion having a first constant diameter for a first predetermined length, said proximal end portion having a second diameter greater than said first constant diameter and sized for leakproof engagement within an aortic artery, said aortic section also having a first plurality of stents attached along said first tubular graft;

a set of iliac sections each having a distal end portion with a third diameter different from the third diameter of any other distal end portion of the iliac sections in the set and at least equal to a fourth constant diameter of a proximal end portion, each iliac section including a second tubular graft including a distal end portion having a third diameter sized for leakproof engagement against an iliac artery, said second tubular graft also including a proximal end portion having a fourth constant diameter for a second predetermined length and approximating said first constant diameter of said distal end portion of said aortic section, said iliac section also having a second plurality of stents attached along said second tubular graft, whereby when said aortic and iliac sections are selected and positioned in an aortic artery and iliac artery, respectively, said proximal end portion of said iliac section and said distal end portion of said aortic section overlap at least a minimum length and engage each other when positioned one within another for said at least minimum length, and an occluder for the other iliac artery whereby the flow of blood to both iliac arteries can be maintained by a bypass graft between the two iliac arteries.

2. A method of repairing a ruptured or symptomatic aneurysm in an aortic artery by a modular stent graft assembly comprising the steps of:

selecting an aortic section from a set of aortic sections each having a proximal end portion with a second diameter different from the second diameter of any other proximal end portion of the aortic sections in the set and greater than a first constant diameter of a distal end portion of the aortic section;

selecting an iliac section from a set of iliac sections each having a distal end portion with a third diameter different from the third diameter of an other distal end portion of the iliac sections in the set and at least equal to a fourth constant diameter of a proximal end portion of the iliac section, inserting in the aortic artery an aortic section of the assembly including a first tubular graft having a proximal end portion and a distal end portion, said distal end portion having a first constant diameter for a first predetermined length, said proximal end portion having a second diameter greater than said first constant diameter and sized for leakproof engagement against an aortic artery, said aortic section also including a first plurality of stents attached along said first tubular graft; and inserting in an iliac artery and into said aortic section an iliac section of the assembly including a second tubular graft including a distal end portion having a third diameter sized for leakproof engagement against an iliac artery, said second tubular graft also including a proximal end portion having a second constant diameter for a second predetermined length and approximating said first constant diameter of said distal end portion of said aortic section, said iliac section also including a second plurality of stents attached along said second tubular graft, whereby when said aortic and iliac sections are selected and positioned in an aortic artery and an iliac artery, respectively, said proximal end portion of said iliac section and said distal end portion of said aortic section overlap at least a minimum length and engage each other when positioned one within another for said at least minimum length, and inserting an occluder in the other iliac artery.

* * * * *